United States Patent [19]

Simons

[11] Patent Number: 4,952,569

[45] Date of Patent: Aug. 28, 1990

[54] ESTRIOL DERIVATIVES

[75] Inventor: Donald M. Simons, Wilmington, Del.

[73] Assignee: E. I. du Pont de Nemours and Company, Wilmington, Del.

[21] Appl. No.: 803,221

[22] Filed: Dec. 2, 1985

[51] Int. Cl.$^5$ .......................... A61K 31/58; C07J 1/00; C07J 17/00; G01N 1/00

[52] U.S. Cl. .................................... 424/88; 540/117; 424/2; 436/533; 514/172

[58] Field of Search ..................... 260/397.5, 239.55 R; 424/2; 514/182, 172; 540/117

[56] References Cited

U.S. PATENT DOCUMENTS 3,940,475  2/1976  Gross ...................................... 424/1

FOREIGN PATENT DOCUMENTS 1006802  10/1965  United Kingdom ............. 260/397.5

OTHER PUBLICATIONS

Dean et al., Steroids Lipids Res., vol. 3, 82–89, (1972).
Walker et al., Steroids, vol. 21, 259–283, (1973).
Da Re et al., Arch. Pharm. (Weinheim), vol. 308(12), 981–982, (1975).

*Primary Examiner*—Joseph A. Lipovsky
*Attorney, Agent, or Firm*—George A. Frank

[57]  ABSTRACT

Estriol and estradiol glycidyl ethers, immunogenic conjugates thereof and processes for their preparation are provided. The immunogenic conjugates are useful for eliciting and purifying antibodies and in performing immunoassays for estriol and estradiol.

6 Claims, No Drawings

ESTRIOL DERIVATIVES

This invention relates to the preparation of new compositions for making immunogenic materials that elicit anti-estriol antibodies and affinity chromatography materials for purification of anti-estriol antibodies. One such composition. 3-(2'.3'-epoxy-propoxy)-1,3,5,(10)-estratrien-16α,17β-diol. is also useful in immunoassays for estriol in biological fluids.

BACKGROUND ART

Estriol [estra-1.3.5(10)-triene-3,16α,17β-triol], an estrogenic hormone, is the predominant steroid hormone most frequently found in the urine of pregnant women. The placenta produces large amounts of this hormone and both serum and urine levels of estriol have been determined in an effort to confirm early stage pregnancy. Monitoring hormone levels continues to indicate the state of fetoplacental function throughout pregnancy. Determinations of 17β-estradiol and estrone [3-hydroxy-estra-1.3.5.(10)-trien-17-one]may assist in evaluation of ovarian function or, in certain circumstances, may be diagnostic for malignancies where normal body functions do not explain increased levels of these hormones. Assays capable of determining levels of estrogenic hormones, therefore, are useful in clinical practice. Moreover, assays which distinguish between estriol and its metabolic precursor 16α-hydroxyestrone are particularly useful in determination of pregnancy at early stages.

Immunoassays have been recognized as having the speed, sensitivity and convenience necessary to provide an assay for serum estriol at levels in the range of 3-50 ng/mL. Antibodies useful for performing such immunoassays are usually elicited by coupling the desired hapten, such as estriol, to a carrier, most often protein, and injecting these materials into an appropriate host. Estriol contains no functional groups that are themselves amine-reactive. It is necessary, therefore, to use some derivative having an amine-reactive group to couple the derivative to carrier proteins. One such derivative prepared by Dean et al., Steroids Lipids Res., Volume 3, 82-89 (1972). was estriol-6-(0-carboxymethyl)oxime which required a four-step synthetic procedure. This synthesis resulted in an overall yield of about 6%, with the most significant losses occurring in the second reaction in the sequence. This reaction produced multiple side reactions from the oxidation of estriol triacetate to 6-oxoestriol triacetate with chromium trioxide. Necessary purification of the product accounted for additional losses. The need for improved synthetic procedures for estriol derivatives is exemplified by the continued work on improving the existing synthetic routes. Two recent reports of improved methods of forming the 6-oxoestratrienes are Garza et al., Steroids, Volume 42, 469-474 (1983) and Schaumann et al . Ger. (East) DD 200,802 (1983).

U.S. Pat. No. 3,940 475 issued Feb. 24, 1976, discloses another estriol derivative used to prepare antibodies to estriol. 4-(p-carboxyphenylazo)estriol or "capaztriol". It was obtained from the reaction of diazotized p-aminobenzoic acid with estriol under alkaline conditions, followed by chromatographic purification resulting in yields of approximately 15-20%.

A series of estriol and estradiol derivatives was prepared by Walker et al.. Steroids. Volume 21, 259-283 (1973) with substituents at the 6-position. These specific 6-oxo derivatives were used to prepare immunogens with carrier proteins and were compared with randomly linked derivatives for their ability to elicit antibodies with minimal cross-reactivity with structurally similar analogs. It was found that random-linkage immunogens of estriol chloroformates with carrier proteins produced antibodies with 30-100% cross-reactivity, while those with a 6-oxo linked estriol had a 1-12% cross-reactivity with estrone and estradiol. This study suggests that linkage through the 6-position led to immunogens capable of producing antibodies with acceptable specificity However, each derivative required extensive complex synthetic procedures for its preparation, diminishing their convenience and utility in the preparation of immunogens; 6-oxoestriol itself was only produced in 11% yield.

Eshhar et al., protides of the Biological Fluids, Volume 29, 823-826 (1982). used four steroid hormone derivatives to elicit immune responses in C57Bl/6 mice whose spleen cells were then fused with myeloma cells to derive hybridomas. The monoclonal antibodies secreted from these hybridomas were tested for reactivity with several steroid hormones and their derivatives by a coated charcoal radioimmunoassay. Immunogens used were estrone-3-glucuronide-BSA, estradiol-6-(0-carboxymethyl)oxime-BSA. estriol-16α-glucuronide-BSA and pregnanediol-3α-glucuronide-BSA. Useful monoclonal antibodies, exhibiting acceptably low cross-reactivity with closely structured analogs, were selected for immunoassays of estrone, estradiol, estriol-16α-glucuronide, and pregnanediol. Eshhar et al. and the references cited therein do not report yields for the synthesis of estradiol-6-(0-carboxymethyl)oxime. Since, however, this compound was prepared by procedures generally utilized, it is expected that yields similar to the very low yields obtained by Dean et al. were achieved.

Da Re, et al., Arch. Pharm. (Weinheim), Volume 308(12), 981-982 (1975), prepared an estrone derivative that was useful as a therapeutic agent for treatment of high blood pressure and other cardiacrelated conditions. Estrone was reacted with epichlorhydrin under basic conditions in ethanol to produce 3-epoxypropoxy-estra-1.3.5(10)-trien-17-one as an intermediate in 72%. The epoxide was then reacted with isopropylamine in benzene to produce the cardioactive 3-(3'-isopropylamino-2'-hydroxypropoxy)-estra-1.3.5(10)-trien-17-one. It is no known whether the epoxide intermediate might be useful as an immunogen, when coupled with a carrier, to elicit high specificity antibodies.

It is recognized that increased immunoassay specificity can be achieved by using conjugates of low molecular weight materials and carrier proteins as immunogens while utilizing conjugates having different linkages as competitive reagents in the immunoassays. It is believed that the antibodies elicited using one linkage would be less likely to react nonspecifically with conjugates having a second, structurally dissimilar linkage. A reduction in nonspecific reactivity can also be achieved by using different carrier proteins for immunogen and assay reagent.

There is a need for steroid derivative preparations and linking chemistries that will permit rapid, efficient, and economical preparation of conjugates of estriol and estradiol with carrier materials. The conjugates so obtained should be useful in eliciting antibodies specific for the hormone or analog used to prepare them and should also be practical to synthesize.

DISCLOSURE OF THE INVENTION

The new compositions of this invention are compounds of the formula shown below, wherein $R_1$=OH or H:

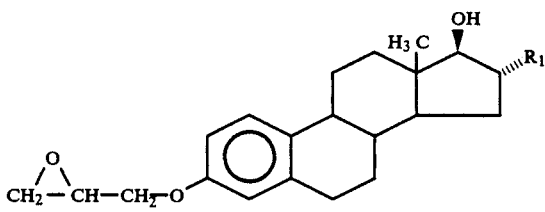

The new compounds can be covalently linked either directly or through an appropriate intermediate molecule to carriers such as proteins, glycoproteins. carbohydrates or solid phases to form immunogenic conjugates. These conjugates can be used for eliciting antibodies by injection into an appropriate host, for purifying antibodies by ligand binding separations. and for performing immunoassays for estriol and estradiol in biological samples.

DESCRIPTION OF THE INVENTION

This invention concerns derivatives of estriol and estradiol which are useful in eliciting antibodies, purifying antibodies with affinity chromatography techniques, and performing immunoassays.

Estriol contains one phenolic hydroxyl group at the 3-position, and two alcoholic hydroxyl groups at the 16-and 17-positions. It has now been found that the phenolic hydroxyl group, when reacted with epichlorohydrin under basic conditions, produces insoluble 3-(2'.3'-epoxypropoxy)-1.3.5.(10)-estratrien-16α, 17β-diol, hereinafter more conveniently called estriol-3-glycidyl ether. This ether, when reacted with various carriers produces hydrolytically and oxidatively stable conjugates. The alcoholic hydroxyl groups remain unchanged by this procedure. The new derivative can be prepared in significantly higher yields than other derivatives previously prepared, such as estriol-6-carboxymethyl oxime (see Dean et al., above). The glycidyl ether is highly reactive with amino groups of proteins and glycoproteins and this reactivity provides the opportunity to prepare covalent conjugates of the glycidyl ether derivative with any desired amino groups which may occur in a protein. The protein can be immobilized on a solid phase or be in solution. The new derivative does not require activation with auxiliary coupling agents, such as carbodiimides, prior to coupling with proteins, allowing more efficient and less laborious coupling procedures (no additional reagents or purification procedures are required).

This single-step derivatization procedure at the 3-position can also be used with estradiol which can be reacted with epichlorohydrin in a manner similar to that with estriol to prepare the glycidyl ether derivative. Epichlorohydrin can be reacted in a 1- to 20-fold molar excess over estriol or estradiol in aqueous alkali at temperatures in the range of 20°-80° C. The reaction can be allowed to continue for from 0.5-3 hours with stirring. The glycidyl ether derivative so produced is insoluble in the alkaline reaction medium, while the unreacted starting materials remain in solution. This differential solubility provides a convenient means for the isolation of product from the reaction medium. Washing with cold aqueous base to remove remaining starting material leads to further purification of the product. Yields from such one-step derivatizations of estriol, for example, were above 95 percent.

The glycidyl ether derivatives of this invention are useful in many aspects of the practice of immunology and immunochemistry. For example, the derivatives can be used to prepare materials capable of eliciting immune response in appropriate animal hosts. It is known that substances having molecular weights less than about 1.000 daltons are usually incapable of eliciting the production of antibodies in immunocompetent hosts. These substances, referred to as haptens, must be coupled with larger substances, called carriers, that render the hapten capable of eliciting an immune response. These carriers can be selected from a variety of substances including proteins, glycoproteins, carbohydrates, latex particles. The hapten-carrier conjugate is capable of elicitinq antibody production in animals having immune systems competent to synthesize antibodies reactive with the haptens. The glycidyl ether derivatives of this invention can react with free amino groups of carrier proteins such as albumins, metalloproteins. and globulins, to produce suitable immunogenic conjugates. These conjugates, or immunogens, are injected into appropriate animal hosts to stimulate the production of antibodies The antibodies so produced can be harvested for direct use in specific binding reactions with the hapten or closely related anologs, or they can be first purified from animal serum by any of several known means such as ammonium sulfate precipitation affinity chromotography with specific binding ligands, protein A.

Alternatively, the immune lymphocytes harvested from the injected host can be screened using the conjugates of this invention to select those cells which are responsive to the derivative-carrier conjugate. These can then be fused with appropriate immortal cells, such as myeloma cells, to produce hybridomas that are capable of producing monoclonal antibodies. Methods of cell fusion, selection, and proliferation used to produce hybridomas are well known and are generally modifications to the procedures of Kohler et al.. Nature. Volume 256, 495-497 (1975).

The antibodies harvested from animal serum (polyclonal) or hybridomas (monoclonal) can be used in specific binding reactions with the hapten derivative. Immunoassays are one category of such specific binding reactions and are well known. They can be performed with the hapten derivative and its specific antibody in a manner that allows an unknown hapten to compete with the hapten derivative or its analog for binding sites on antibody. These reactions may occur in solution, or with antibody or hapten derivative immobilized to an appropriate solid phase. The latter configuration is most convenient when a separation of unreacted reagent(s) is desirable. They can also be performed in a non-competitive mode using an excess of labelled specific antibody to react with the unknown hapten. In this approach the hapten derivative is attached to a solid support and used to remove any unbound labelled specific antibody. The amount of label remaining in solution or bound to the solid may be measured as an indication of the amount of unknown hapten present.

Another utility of specific binding reactions with the compounds of this invention is harvesting antibodies or cell surface receptors reactive with an immobilized hapten derivative. Preparation procedures for antibodies frequently require purification from complex solutions containing undesired proteins, nucleic acids, lipids, cell debris, etc. A rapid, specific, and efficient means to perform these purifications is to immobilize hapten derivatives onto an appropriate solid phase and to react the hapten derivatives with their antibodies under conditions that allow binding to occur. The immobilized antibody can then be removed from the unwanted constituents in solution washed to remove additional unbound material from the solid phase, and then eluted using known means such as with soluble hapten derivative or analog, mild acid, chaotropic agent, etc. These purified antibodies can then be used in immunoassays or cell receptor binding assays as is or after they have been labelled with a reporter substance, such as a radioisotope enzyme, fluorescent or chemiluminescent molecule. If the antibody is labelled with a reporter, a second purification with immobilized hapten derivative is advantageous in separating labelled antibody from free, unreacted label. The free label can be washed from the solid phase and the labelled antibody removed from the hapten derivative by known means. This purification process is most convenient when the hapten is immobilized onto solid phases which can be easily packed into a chromatographic column, such as crosslinked dextran, agearose, silica gel, controlledpore glass beads, that have been functionalized on their surfaces with a free amine group. However, the process of purification can also be carried out with the glycidyl ethers immobilized onto any surface accessible to solutions containing binding agents to be purified. This process is known as affinity or ligand chromatography.

The estriol and estradiol derivatives of this invention can be reacted directly with tree amino groups available on proteins, glycoproteins aminofunctional latex particles etc., or they can be first reacted with another molecule having a second functional group such as ethyl 3-mercaptopropionate. The product resulting from this reaction has a carboxyl functional group after hydrolysis, and is reactive with crosslinking agents such as the carbodiimides.

The following examples illustrate the invention:

EXAMPLE 1

SYNTHESIS OF ESTRIOL-3-GLYCIDYL ETHER

A 2.01 g quantity of estriol (6.97 mmoles) was placed in a 25 mL flask equipped with a mechanical stirrer, and 0.293 q solid sodium hydroxide (7.21 mmoles), 0.75 mL water and 10 mL epichlorohydrin (11.8g.127 mmoles) were added in that order. The mixture was stirred for 45 minutes while the flask was immersed in an oil bath heated to about 80° C. The mixture was then cooled by immersing the flask in an ice bath for a few minutes. The unreacted epichlorhydrin was removed by evaporation under reduced pressure over a period sufficient to produce a dry solid. The solid residue was triturated with cold 0.1 N sodium hydroxide and the resulting suspension filtered. The product was washed with water until the filtrate was neutral and the washed product was dried in a vacuum desiccator. The yield was 2.38 g or 99% yield of theoretical.

The product was analyzed by infrared and nuclear magnetic resonance techniques and the results were consistent with the claimed structure $R_1$=OH.

EXAMPLE 2

Purification of Anti-Estriol Antibodies Using Affinity Chromotography with Estriol-3-Glycidyl Ether

A. Conjugation of Estriol-3-Glycidyl Ether (E-3-GE) to Human Serum Albumin (HSA)

A 1.467-g quantity of the E-3-GE prepared as in Example 1 was dissolved in 5 mL of a dimethylsulfoxide: dimethylformamide (60:40) solvent and the solution added slowly with stirring to 200 mL of a 100 mg/mL solution of HSA (Fraction V; Sigma Chemical Co.) in a 500 mL flask equipped with a magnetic stirrer. This represented an approximately 25-fold molar excess of E-3-GE over HSA. A white precipitate was formed and stirring was continued at 4° C. overnight. The solution pH was adjusted from 7.1 to 10 0 with 0.5N NaOH and 5 mL of dimethylsulfoxide was added with stirring. The reaction mixture was dialyzeo overnight at 4° C. against 4 liters pBS buffer (0.06 M NaCl, 0.075 M $NaH_2pO_4$ 0.0014M KCl. pH 7.4). using an 8,000 molecular weight cut-off dialysis tubing. Dialysis was continued with 2 changes of 4 liters each of pBS buffer (diluted 1:2 from above) at 4° C.

The white precipitate persisted through the dialysis procedure and was removed by filtration. The filtrate was lyophilized and the product, E-3-GE/HSA conjugate was stored at 4° C in a sealed container.

B. Coupling of E 3-GE/HSA Conjugate to Crosslinked Agarose

E-3-GE/HSA conjugate solution was prepared by dissolving 300 mg lyophilized E-3-GE/HSA, prepared as in Example 2A. in 12 mL or 20 mM N-2-hydroxyethyl-piperazine-N'-2-ethanesulfonic acid buffer (HEPES), pH 7 2, in a 50 mL screw-capped test tube. This conjugate solution was slowly added to a 50-mL screw capped test tube containing 12 mL Affi-Gel ®10 resin (Bio-Rad Laboratories). which had been previously washed 3 times with cold distilled water. The mixture was allowed to rock tor 1 hour at room temperature on a rocking platform to facilitate the coupling of the conjugate with the N-hydroxy succinimide groups on the resin. A 1.2-mL volume of 1M ethanolamine was added to the tube to block remaining uncomplexed resin sites and the tube rocked for 1 hour at room temperature.

The complexed resin was washed on a sintered glass funnel with 5 volumes or 20 mM HEPES buffer. The resin was stored in 30 mL 20 mM HEPES buffer, pH 7.2.

C. Affinity purification of Anti-Estriol Antibody

A 2-mL volume of the resin prepared in Example 2B was packed into a 0.75 x 10 cm Econo-column ® (BioRad Laboratories) and washed sequentially with 5 bed volumes of pBS buffer (0.12 M NaCl. 0.15 M $NaH_2pO_4$, volumes and 0.0027M KCl pH 7 4). 5 bed volumes of 6M guanidine HCl, followed by 5 bed volumes of PBS buffer. Two mL of polyclonal anti-estriol antibody, which had been produced in rabbits from immunizations with estriol-6-carboxymethyloxime-KLH and separated from whole antiserum using an Affi-gel Blue ® column (Pharmacia Fine Chemicals), was placed on the affinity column prepared above. The antibody solution was followed by 1 mL of pBS and a single 3 mL fraction was collected. Two mL of 3M $NH_4SCN$ was then used to elute anti-estriol antibodies bound to the estriol conjugate immobilized on the column resin. Aliquots of the eluted fractions and the Affi-gel Blue ® purified starting material were spiked with a myoglobin standard solution and analyzed by HPLC using a Zorbax ® Bio Series GF-250 size exclusion column (a registered trademark of E. I. du Pont de Nemours and Company). The peak heights of the antibody were compared to the peak heights of the myoglobin internal standards to determine an (IgG) antibody:myoglobin ratio for each eluted fraction. The peak ratios and calculated recoveries ar ® presented in Table 1 together with the results of similar experiments using derivatives known from the prior art [these known derivatives were prepared by the process of Example 2(B)]:

TABLE 1

| Antibody | Peak Ratio (Antibody:Myoglobin) | % Antibody Recovered |
| --- | --- | --- |
| Whole antiserum (treated with Affi-Gel Blue) | 2.11 | — |
| E-3-GE/HSA resin purified | 0.15 | 7.3 |
| "capaztriol"/HSA resin purified | 0.19 | 9.1 |
| E-6-CMO/HSA resin purified | 0.13 | 6.3 |

The utility of the derivatives of this invention is indicated by the comparable recoveries obtained with these derivatives and the known but difficultly synthesized derivatives of the prior art.

EXAMPLE 3

Inhibition Immunoassay for Estriol Using E-3-GE/HSA Solid Phase A. Solid Phase Preparation The E-3-GE/HSA conjugate prepared in Example 2A was immobilized on 96 well polystyrene microtiter plates (Immulon II). Plates were rinsed with distilled water five times, and 100μL of a 100 μg/mL solution of the conjugate in a 0.15M NaCl. 0.01M $NaH_{2p}O_4$ (pH 9.0) solution (wash buffer) was added to each plate well. This solution was allowed to incubate for approximately 16 hours at 4° C. before each cell was washed five times with wash buffer adjusted to pH 7.8. Control plates to determine levels of nonspecific binding were prepared by substituting a 50 μg/mL HSA solution for the E-3-GE/HSA solution. Excess fluid was blotted from the plates, 200 μL of a diluting buffer [0.5M NaCl, 0.01 M $NaH_2pO_4$. 0.05% Triton X-100, and 1% human serum albumin (Fraction V; Miles Laboratories)]. pH 9.0. was added to each well, the plates were covered with plastic wrap and allowed to incubate for 90 minutes at room temperature. This treatment blocked any remaining adsorptive sites in plate wells not occupied by the conjugate to prevent the nonspecific adsorption of reagents subsequently added. Finally, plate wells were washed five times with wash buffer, the plates blotted of excess moisture, and stored at 4° C.in a covered plastic container B. Estriol Inhibition of Rabbit Anti-Estriol Antibody Binding to E-3-GE/HSA Conjugate Both E-3-GE/HSA-coated and the HSA-coated control plates prepared in Example 3A were used to determine the ability of E-3-GE/HSA to bind anti-estriol antibody in the presence of estriol. Estriol was first dissolved in methanol at 1 mg/mL and then diluted to levels of 100 and 10,000 ng/mL in distilled water. A 15-μL volume was placed in four wells for each estriol level on both an HSA- and an antigencoated plate. An anti-estriol antibody (raised against estriol-6-carboxymethyloxime-KLH immunogen) was diluted 1:8 in the diluting buffer and 25μL of this dilution was added to each plate well containing estriol solution. A 25-μL volume of the diluted antibody was also added to plate wells that contained no estriol to determine both maximum antibody binding to antigen plate wells and nonspecific binding to HSA plate wells. The combined antibody-estriol mixture was incubated in plastic wrap covered plates for one hour at 37° C. plates were washed five times with pH 7.8 Wash buffer and 100μL anti-rabbit IgG conjugated to horse radish peroxidase (Miles Laboratories; diluted 1:300 with pH 7.8 diluent) was added to each well. Covered plates were incubated for one hour at room temperature and then washed six times with the pH 7.8 wash buffer. The plates were blotted to remove excess moisture between each wash. After the last wash. 100μL of a solution 40 mM in 2,2'-azino-bis (3-ethylbenzthiazoline sulfonic acid) and 0.3% in hydrogen peroxide in 0.05M citric acid buffer (pH 4.0) was added to each plate well and the covered plates incubated for 20 minutes at room temperature. This substrate solution should not be prepared more than 15 minutes prior to use. After the 20-minute development period, the absorbances at 410 nm of the solutions in each plate well were determined using a semi-automated microtiter plate spectrophotometer (Dynatech Laboratories, Inc; Model MR 600) with the results presented in Table 2:

TABLE 2

ESTRIOL INHIBITION OF ANTI-ESTRIOL BINDING TO ESTRIOL-3-GLYCIDYL HSA IMMOBILIZED ON MICROTITER PLATES

| Estriol Concentration (ng/mL) | Absorbance (at 410 nm) | |
| --- | --- | --- |
| | E-3-GE/HSA ($\bar{x}$; n = 4) | HSA ($\bar{x}$; n = 4) |
| 0 | 1.17 | 0.21 |
| 100 | 0.65 | 0.18 |
| 10,000 | 0.10 | 0.22 |

The results indicate that anti-estriol antibodies, elicited in rabbits with an estriol-6-CMO-KLH immunogen, will bind to E-3-GE/HSA immobilized on a polystyrene microtiter plate, that estriol in solution diminishes that binding, and that the estriol conjugates of this invention are useful in immunoassays for estriol.

I claim:

1. Compounds of the formula

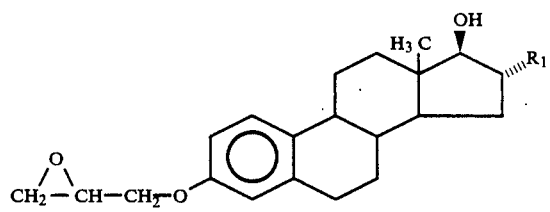

wherein $R_1$ is H or OH.

2. An immunogenic conjugate of compounds of the formula

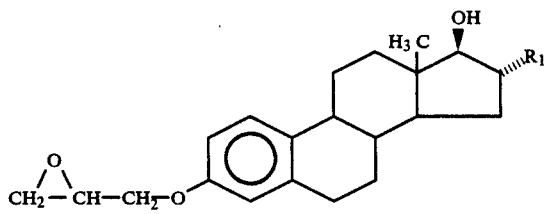

and a carrier, wherein $R_1$ is H or OH.

3. The conjugate of claim 2 wherein the carrier is selected from the group consisting of proteins, glycoproteins, carbohydrates and latex particles.

4. The conjugates of claim 2 wherein the carrier is linked to the compound through an intermediate molecule.

5. An immunoassay for estriol comprising the steps of immobilizing the immunogenic conjugate of claim 2 on a solid phase followed by carrying out any known immunoassay protocol.

6. A process for eliciting anti-estriol antibodies in standard immunization protocols utilizing the immunogenic conjugate of claim 2.

* * * * *